(12) United States Patent
Rothfuss et al.

(10) Patent No.: US 10,016,240 B2
(45) Date of Patent: Jul. 10, 2018

(54) INSTRUMENT

(71) Applicant: gomtec GmbH, Seefeld (DE)

(72) Inventors: Patrick Rothfuss, Hallbergmoos (DE); Bernd Gombert, Wörthsee (DE); Bartolomiej Stanczyk, München (DE)

(73) Assignee: gomtec GmbH, Seefeld (DE)

( * ) Notice: Subject to any disclaimer, the term of this patent is extended or adjusted under 35 U.S.C. 154(b) by 405 days.

(21) Appl. No.: 14/751,573

(22) Filed: Jun. 26, 2015

(65) Prior Publication Data
US 2016/0016320 A1 Jan. 21, 2016

(30) Foreign Application Priority Data

Jul. 4, 2014 (DE) ........................ 10 2014 009 891

(51) Int. Cl.
A61B 34/30 (2016.01)
A61B 19/00 (2006.01)
A61B 34/00 (2016.01)
A61B 17/00 (2006.01)

(52) U.S. Cl.
CPC .......... *A61B 19/2203* (2013.01); *A61B 34/30* (2016.02); *A61B 2017/00477* (2013.01); *A61B 2034/305* (2016.02); *A61B 2034/715* (2016.02)

(58) Field of Classification Search
CPC ................ A61B 19/2203; A61B 34/30; A61B 2034/305; A61B 2034/715
See application file for complete search history.

(56) References Cited

U.S. PATENT DOCUMENTS

| 5,104,005 A * | 4/1992 | Schneider, Jr. ... B05C 17/00553 222/137 |
| 5,313,852 A * | 5/1994 | Arena ................. F16H 25/2018 74/89.13 |
| 5,673,593 A * | 10/1997 | Lafferty .............. F16H 25/2015 192/141 |
| 5,685,390 A * | 11/1997 | Chikuma ............. B62D 5/0448 180/444 |
| 5,735,174 A * | 4/1998 | Enomoto ................ F16C 29/02 74/89.32 |
| 7,316,681 B2 | 1/2008 | Madhani et al. |
| 8,365,633 B2 * | 2/2013 | Simaan .............. A61B 19/2203 600/141 |
| 2008/0282821 A1 * | 11/2008 | Tokumitsu ............... B25J 9/042 74/29 |
| 2009/0247364 A1 * | 10/2009 | Sano ..................... B60T 13/746 477/197 |
| 2014/0298933 A1 * | 10/2014 | Kohlmeyer ............. F16H 25/20 74/89.32 |
| 2016/0089121 A1 * | 3/2016 | Stand, III ........... A61B 10/0275 600/567 |

* cited by examiner

*Primary Examiner* — David M Fenstermacher

(57) ABSTRACT

The invention relates to an instrument (30) with an elongated first shaft (42), an end effector which is arranged on a distal end of the first shaft (42) and an actuation unit (19) arranged on the proximal end of the first shaft, wherein the actuation unit (19) comprises a first wheel (32) which is connected non-rotatably with the first shaft (42). The first shaft (42) is axially displaceable in relation to the first wheel (32) and is in threaded engagement with a second wheel (33) which is axially immovable in relation to the first wheel (32).

17 Claims, 9 Drawing Sheets

|  | Wheel | | | | Shaft (sleeve) | | |
|---|---|---|---|---|---|---|---|
|  | 31 | 32 | 33 | 34 | 41 | 42 | 44 |
| Actuation of grippers 64, 65 | X |  |  |  | R |  |  |
| Swivelling of end effector 60 |  |  | X |  | A | A |  |
| Rotation of end effector 60 | X | X | X |  | R | R |  |
| Rotation of swivel mechanism 79 |  |  |  | X |  |  | R |
Fig. 10
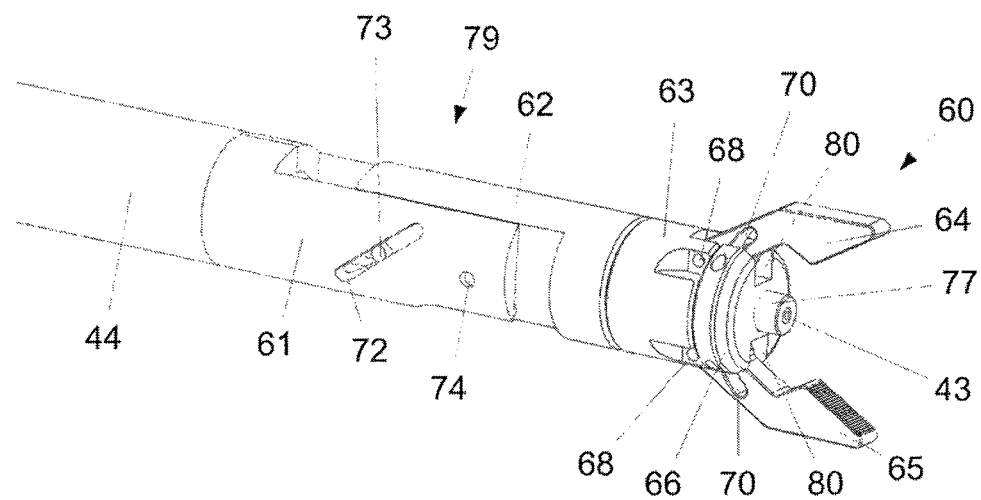
Fig. 11
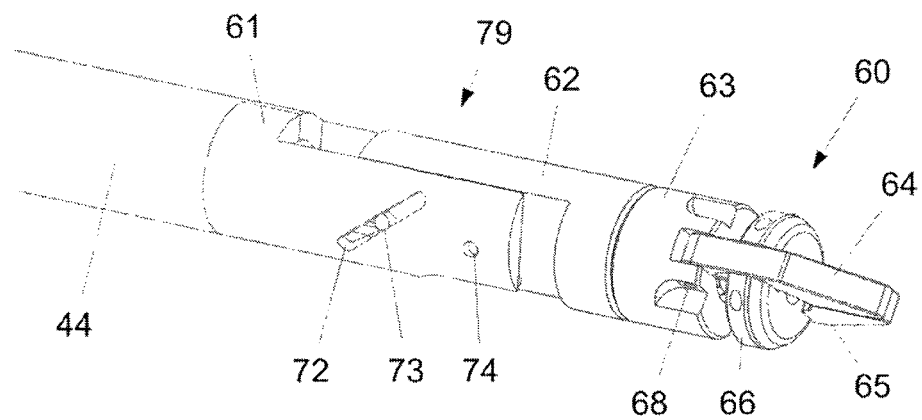
Fig. 12

INSTRUMENT

The invention relates to a replaceable instrument for use with a robot.

The publication U.S. Pat. No. 7,316,681 discloses a surgical instrument intended for use in connection with a surgical robot in order to perform surgical procedures on a patient. The instrument has an actuation unit by means of which an end effector located on the end of an instrument shaft can be displaced. The displacing forces are transmitted from the actuation unit to the end effector via several cables running within the instrument shaft which are deflected via several pulleys.

This cable mechanism disclosed in U.S. Pat. No. 7,316,681 is relatively complex in structure and requires high precision in manufacture. The cable mechanism also requires a specific pre-tensioning of the individual cables. However, the pre-tensioning can slacken over the course of time, for which reason the instrument needs to be checked regularly in order to ensure perfect operation.

The problem addressed by the invention is to create an instrument with a transmission mechanism which is distinguished through a simple and maintenance-friendly design and which dispenses with the use of cables as transmission elements requiring pre-tensioning.

The problem is solved through an instrument with an elongated first shaft, an end effector which is arranged on a distal end of the first shaft and an actuation unit arranged on the proximal end of the first shaft, wherein the actuation unit comprises a first wheel which is connected non-rotatably with the first shaft, wherein the first shaft is axially displaceable in relation to the first wheel and is in threaded engagement with a second wheel which is axially immovable in relation to the first wheel.

The forces required for actuation of the end effector are transmitted directly from the actuation unit via the first shaft. The first and the second wheel can be driven independently of one another and permit a movement of the first shaft in two different degrees of freedom. A torque can be transferred to the first shaft via the connection, non-rotatable but freely moveable in an axial direction, with the first wheel, causing said first shaft to rotate around its axis. The threaded engagement between the second wheel and the first shaft translates a rotary relative movement between the first shaft and the second wheel into an axial movement of the first shaft along its axis. In this way, the first shaft can for example be moved axially if the second wheel is driven while the first wheel remains stationary, and it can be rotated if the first and second wheel are rotated together.

The instrument can have a shaft sleeve which surrounds the first shaft, so that the first shaft extends through the shaft sleeve.

The shaft sleeve is connected at its proximal end, rotatably but axially immovably, with one of the two wheels, and can be rotated in relation to both the first shaft and also the first and second wheels.

The end effector is coupled on the distal ends of the first shaft and the shaft sleeve in order to swivel around a swivel axis oriented transversely to the shaft sleeve by means of a swivel mechanism. The end effector can be driven through a relative movement between the first shaft and the shaft sleeve.

The first shaft advantageously has a flexible region which extends at least partially through the swivel mechanism and which follows a swivelling movement of the swivel mechanism. The flexible region is preferably elastic, so that a restoring force caused through the elasticity is exerted on the swivel mechanism and forces this into a clearly defined position, despite any play which may be present.

The shaft sleeve can, in contrast to the first shaft, be completely rigid in design.

In addition to the swivelling movement, the end effector can rotate around an axis of rotation which is swivelable around the swivel axis, referred to here as the end effector axis.

The rotary movement which lends the end effector a second degree of freedom is advantageously controlled through a rotation of the first shaft.

For this purpose, the connection of the end effector with a distal member of the swivel mechanism can be equipped with a corresponding bearing.

The swivel mechanism can comprise a proximal member solidly connected with the distal end of the shaft sleeve and a distal member connected with the first shaft. The distal member (and with it the end effector) can be driven in a swivelling action through an axial displacement of the first shaft relative to the shaft sleeve or the proximal member.

The proximal member can be integrally connected with the shaft sleeve.

The connection of the first shaft with the distal member can be made indirectly in that the first shaft passes completely through the swivel mechanism and is rigidly connected with the end effector.

The swivel mechanism preferably has a guide slot system via which the distal member and the proximal member are moveably connected with one another. One of the two members has at least one guide slot in which at least one bolt of the other member can slide in order to guide the swivelling movement. For example, the proximal member can include the guide slot and the distal member the bolt, or vice versa.

Preferably, one of the two members of the swivel mechanism has two legs between which the other member engages, and the guide slot system comprises two bolts projecting in opposite directions on one of the two members, and on the other member two guide slots, each of which receives one of the bolts.

In order to provide the swivel mechanism with increased stability, two guide slot systems can be arranged, spaced apart axially, on the swivel mechanism. In particular, the distal member can include the bolts of one of the guide slot systems and the guide slots of the other guide slot system, while the proximal member includes the guide slots of one guide slot system and the bolts of the other.

The course of the guide slot(s) determines how the distal member is swivelled in relation to the proximal member in response to an axial displacement through the first shaft. For example, the guide slot can be curved or can run obliquely to the longitudinal axis.

The actuation unit of the instrument preferably possesses a third wheel which is connected, non-rotatably and axially immovably, with the shaft sleeve. Thus, a torque can be transmitted from the third wheel to the shaft sleeve, and the shaft sleeve can be rotated around the longitudinal axis of the instrument through rotation of the third wheel. The end effector, connected with the shaft sleeve by means of the swivel mechanism, can also be rotated around the longitudinal axis through the rotation of the shaft sleeve. The end effector is thus provided with an additional degree of freedom.

The first shaft can be hollow in order to allow a second shaft for driving a working movement of the end effector to be guided therein. For example, the second shaft can be used to actuate one or several grippers of the end effector in order to grasp and hold a particular object or release it again.

In order to actuate the second shaft, the second shaft can be coupled with a fourth wheel of the actuation unit.

Said coupling is preferably non-rotatable and makes possible a transmission of a torque from the fourth wheel to the second shaft. The second shaft should be coupled with the first shaft such that when an axial movement is performed it moves together with the first shaft.

In order to be able to follow the movement of the first shaft without taking along the fourth wheel, the second shaft is preferably mounted in the fourth wheel in an axially displaceable manner. For example, the first and the second shaft can be connected together via a roller bearing in order to create a fixed axial connection between the two shafts while simultaneously permitting a rotary relative movement.

The second shaft advantageously has a flexible region of which at least a part extends through the swivel mechanism. The second shaft can then follow a swivelling movement of the swivel mechanism. The flexible region is preferably elastically deformable.

The wheels of the actuation unit should be mounted so as to be axially immovable yet rotatable in relation to one another. Preferably, the wheels are arranged next to one another along a common axis of rotation. For this purpose, at least two of the wheels can be coupled together via a roller bearing.

Radial bearings with an outer ring and an inner ring can be chosen as roller bearings, wherein the outer ring is accommodated in one of the two wheels and the inner ring is pushed onto the other wheel.

The wheels can each be driven by a drive. In order to transmit the driving force of a drive to one of the wheels, the wheel can have a structure distributed on the periphery which transmits the driving force. This structure can overlap in an axial direction with the roller bearing.

The structure can be in the form of gear teeth with which a pinion of the drive meshes. Alternatively, other friction-locking or form-locking structures known to the skilled person can be used.

In an advantageous embodiment of the invention, the structure comprises ferromagnetic bodies which connect with a corresponding drive element of the drive via a magnetic positive connection. According to the invention, the ferromagnetic bodies can consist of magnetisable but not permanently magnetic material, or they can be permanent magnets.

If the instrument is to be used for medical applications, in particular in minimally invasive surgery, the actuation unit can be enclosed by a germ-proof, in particular sterile sleeve-formed barrier. If the wheels of the actuation unit are connected with their drives by means of a magnetic positive connection, the barrier can be arranged in the air gap between the wheels and the corresponding drives.

The drive unit can for example have a cavity into which the actuation unit of the instrument can be inserted, detachably, in the longitudinal direction of the shaft. In order to transmit driving forces from the drive unit to the actuation unit, the drive unit can have several drive modules arranged in a staggered manner in the longitudinal direction, each of which interacts with one of the wheels. For example, a drive module can possess a motor-driveable magnetic ring equipped with permanent magnets which surrounds a corresponding wheel of the actuation unit and which forms a magnetic positive connection with the ferromagnetic bodies distributed on the periphery thereof, so that a torque is transmitted from the magnetic ring to the wheel.

Other features and advantages of the invention are explained in the following description of exemplary embodiments with reference to the attached figures, in which.

Figure 6:
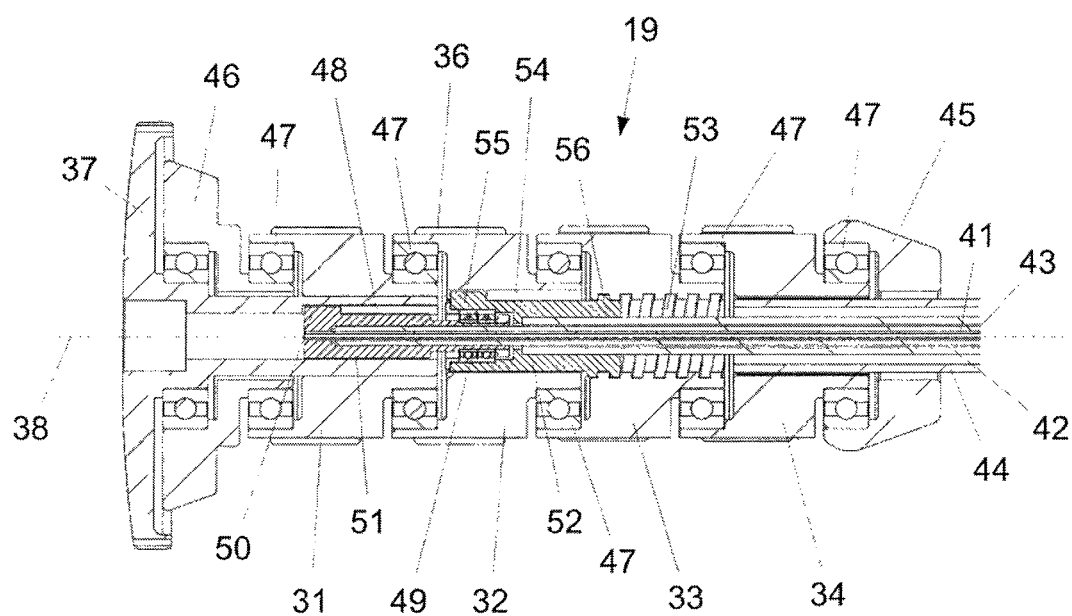
Figure 7:
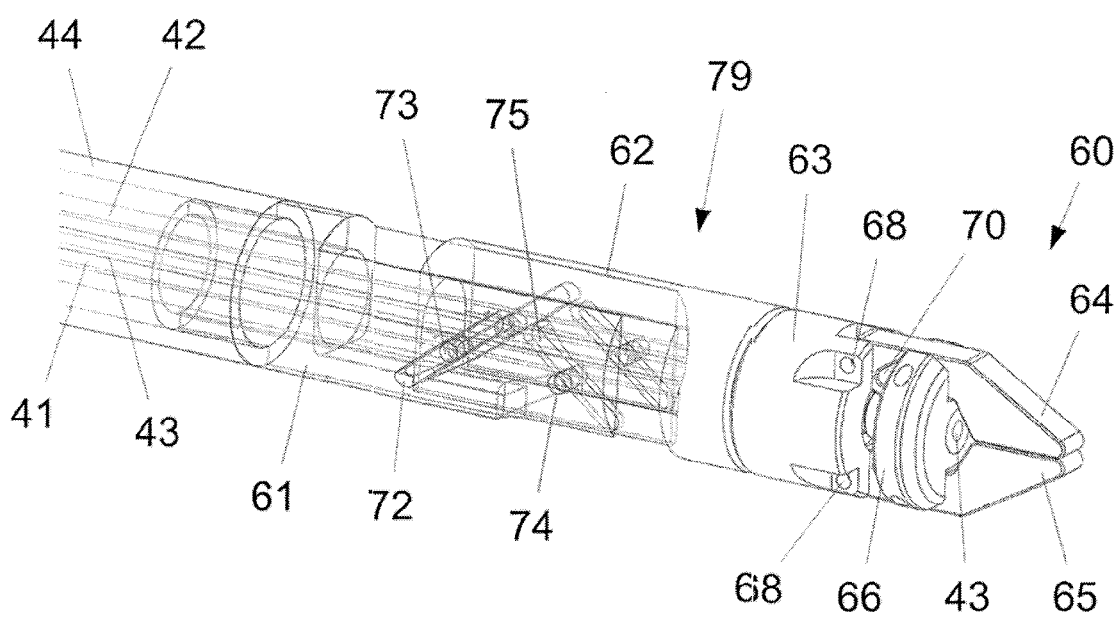
Figure 8:
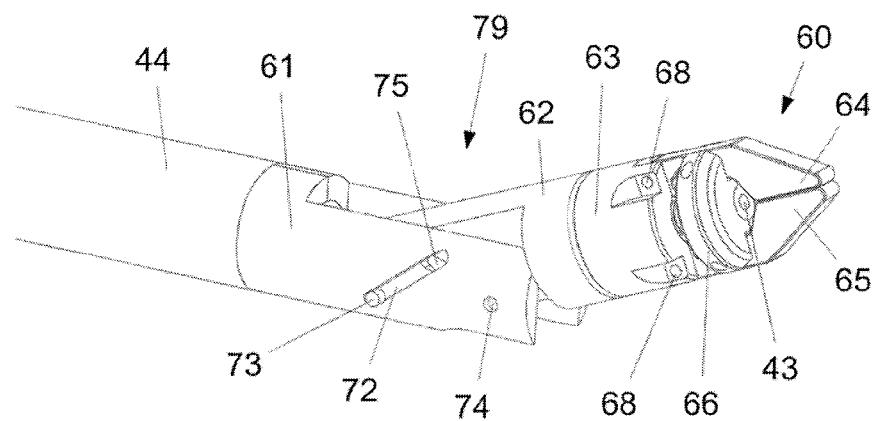
Figure 9:
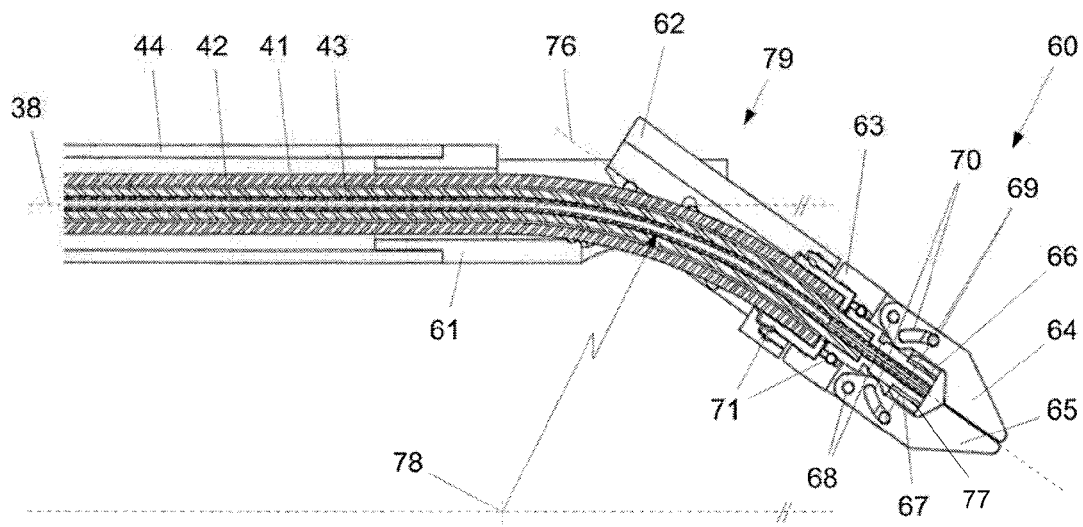
Figure 13:
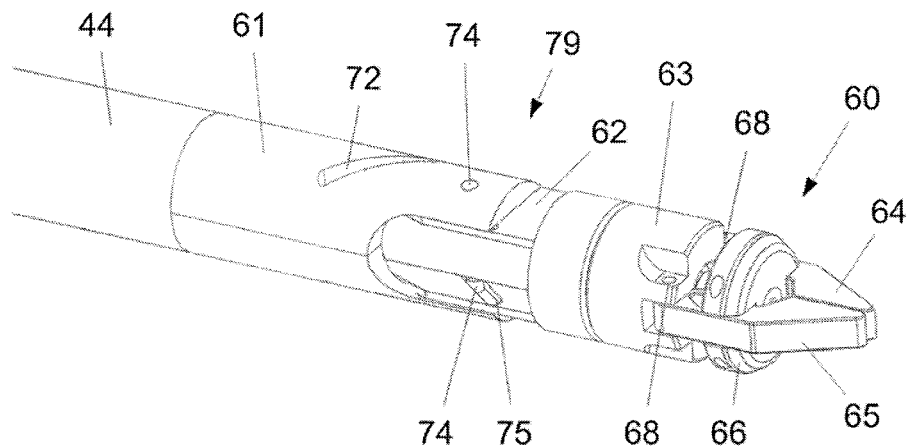
Figure 14:
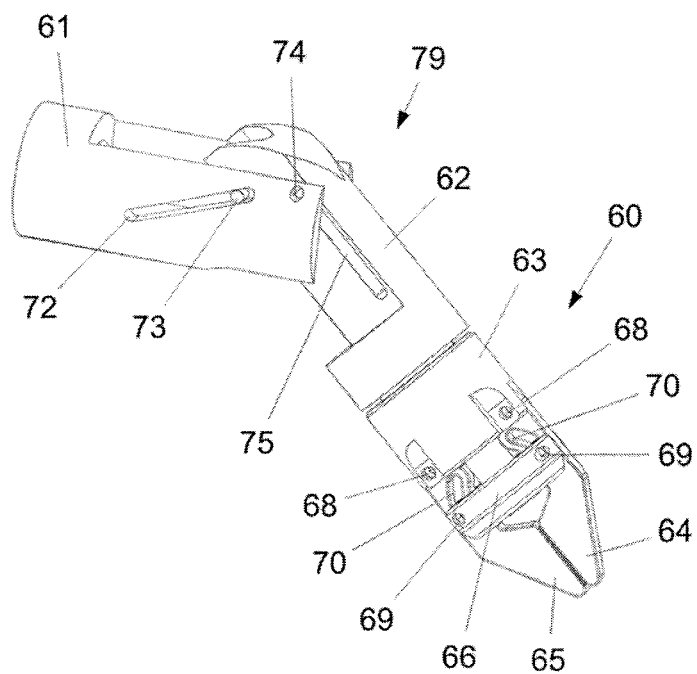
Figure 15:
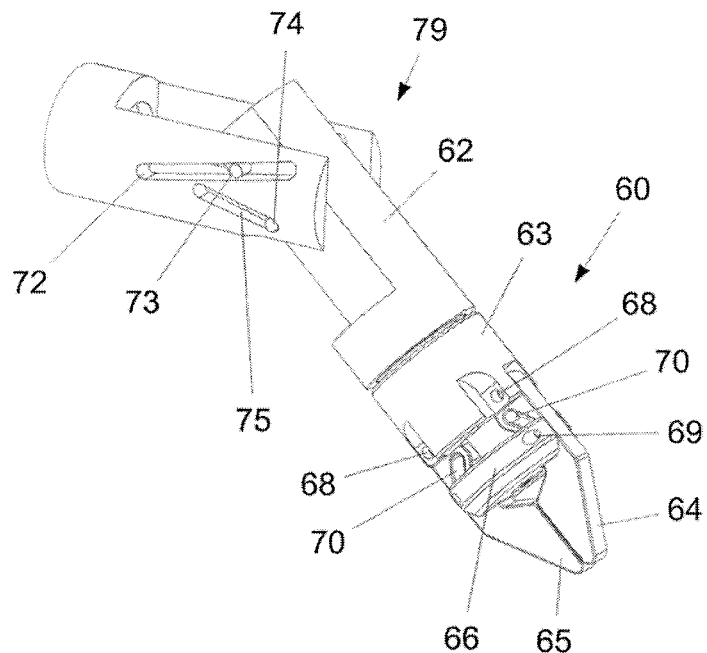
Figure 16:
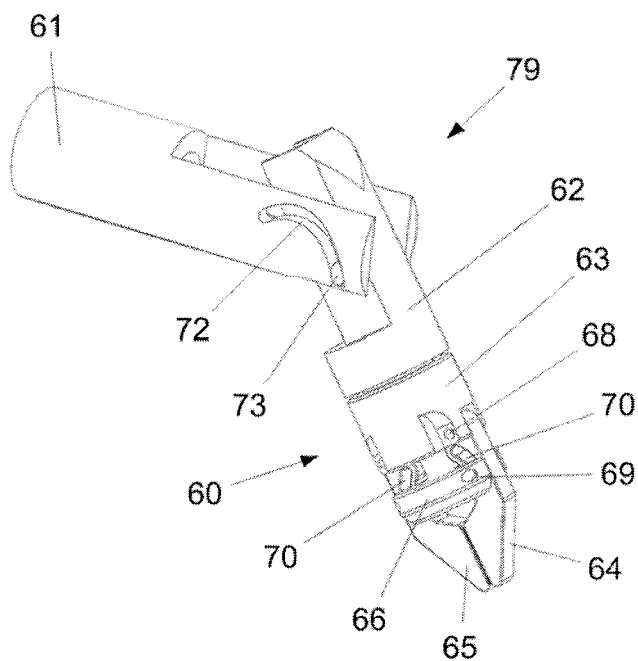

FIG. 6 shows a cross section of an actuation unit on the proximal end of the instrument, FIG. 7 shows a distal end of the instrument with a swivel mechanism and an end effector in extended position, FIG. 8 shows the distal end of the instrument shown in FIG. 7 in angled position, FIG. 9 shows a cross section of the distal end of the instrument, FIG. 10 shows an overview in table form of the possible ways of actuating the instrument;

FIG. 11 shows the distal end of the instrument with grippers of the end effector in opened position;

FIG. 12 shows the distal end of the instrument with the end effector rotated in relation to the swivel mechanism;

FIG. 13 shows the distal end rotated around the longitudinal axis of the instrument;

FIG. 14 shows a distal end with a second embodiment of the swivel mechanism;

FIG. 15 shows a distal end with a third embodiment of the swivel mechanism;

FIG. 16 shows a distal end with a fourth embodiment of the swivel mechanism.

Figure 1:
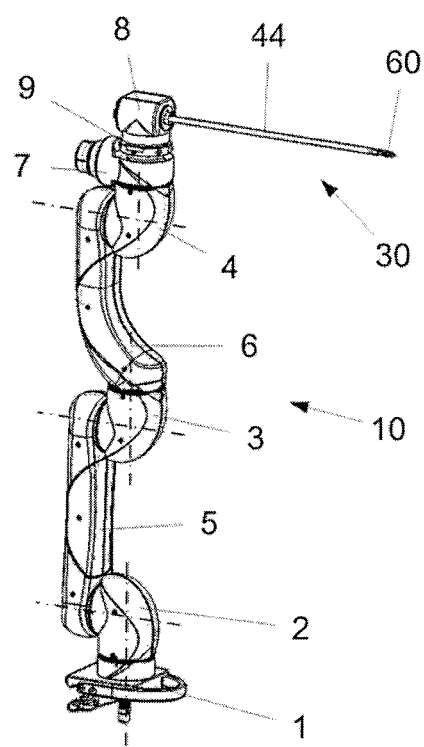
FIG. 1 shows a robot equipped with an instrument.

FIG. 1 shows a robot 10 and an instrument 30 coupled with the robot 10. The robot 10 comprises an attachment element 1, which serves to attach the robot 10 to any suitable object. The attachment element 1 connects with a joint 2 which rotatably connects an arm element 5 with the attachment element 1. A second arm element 6 is connected rotatably with the arm element 5 via a joint 3. Connected to the arm element 6 via a further joint 4 is an input device 7 which allows the user to control the robot 10 and/or the instrument 30.

Each of the three joints 2, 3 and 4 has two axes of rotation oriented at right angles to each other, so that a rotary movement is possible on two connection sides of a joint. The robot 10 can thus be moved in six degrees of freedom. In order to allow corresponding control of the robot 10 the input device 7 preferably has a cap which can also be moved manually in six degrees of freedom. A more detailed explanation of such a robot control system can be found in the applicant's as yet unpublished patent application DE102013019869.

A distal end of the robot 10 is formed by a drive unit 8 which is firmly connected with the input device 7 via a flange 9. The instrument 30 can be coupled, replaceably, with the drive unit 8 and driven or actuated via the drive unit 8.

Figure 2:
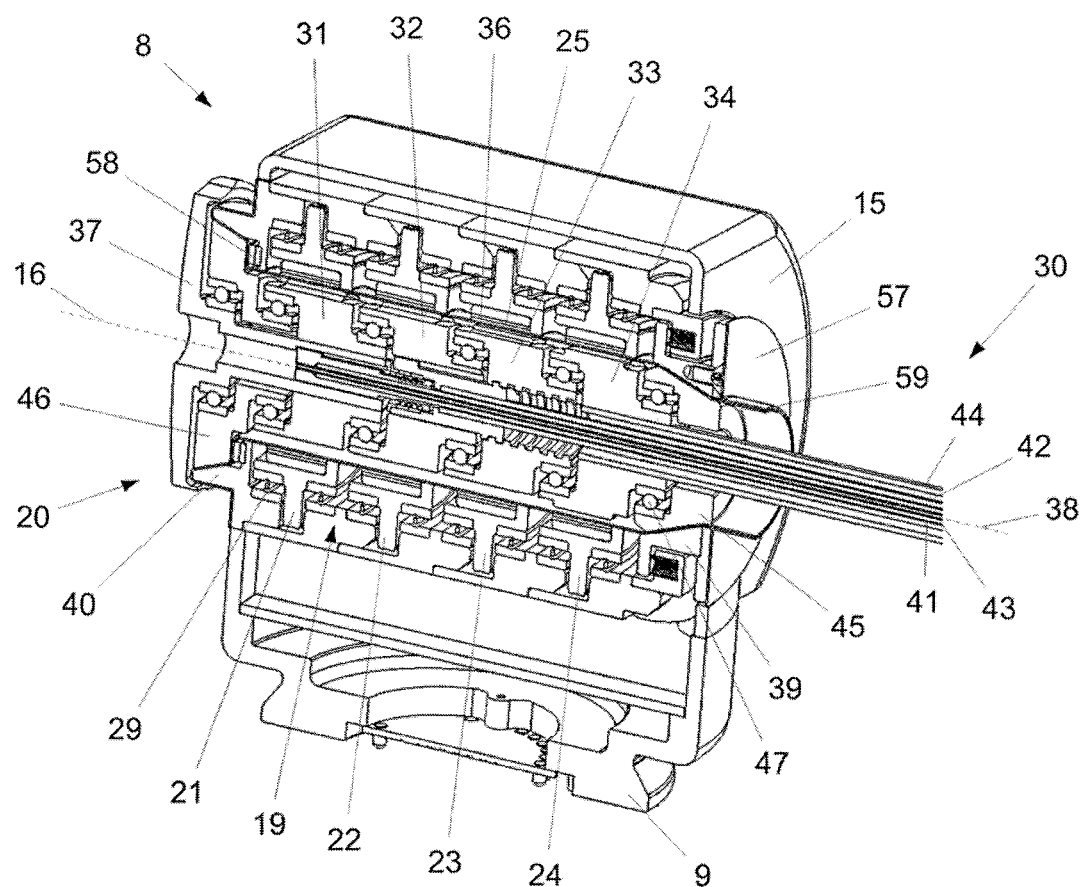
FIG. 2 shows a cross section through a drive unit with an inserted instrument.
Figure 3:
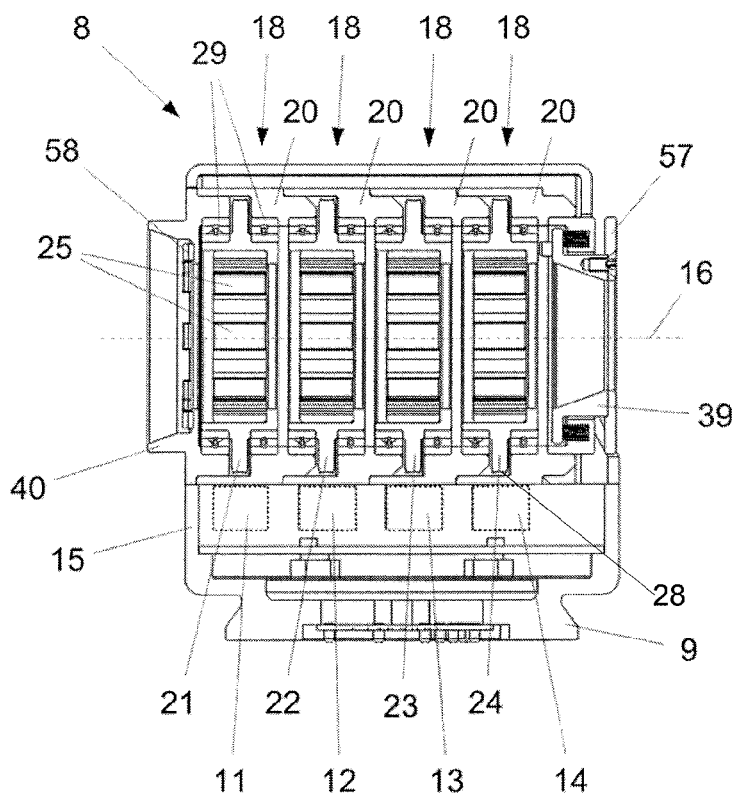
FIG. 3 shows a cross section through the drive unit without the instrument.
Figure 4:
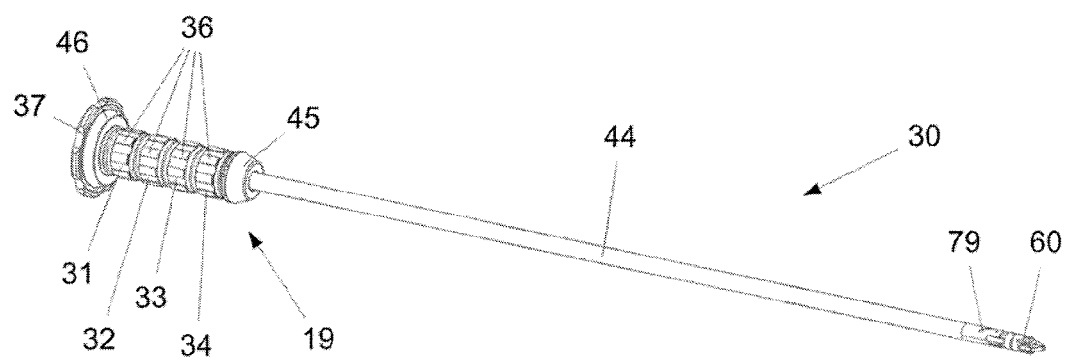
FIG. 4 shows the instrument.

FIG. 2 shows the drive unit 8 with the inserted instrument 30 in cross section, FIG. 3 shows the drive unit 8 without the instrument in cross section, and FIG. 4 shows the instrument 30 detached from the drive unit 8.

The instrument 30 possesses an actuation unit 19 with four wheels 31, 32, 33 and 34, a base element 46 adjacent, on the left, the left-hand outer wheel 31 and a support element 45 adjacent, on the right, the right-hand outer wheel 34. The wheels 31, 32, 33 and 34 are rotatable in relation to one another and in relation to the base and support elements 45, 46 in order to drive movements of an end effector 60 connected with a shaft sleeve 44 by means of a swivel mechanism 79. The base element 46 and the support element 45 are formed so as to taper conically in the direction of the end effector 60.

The drive unit 8 has a housing 15 which is firmly connected with the flange 9. The drive unit 8 is hollow throughout along an axis 16, so that the instrument 30 can be inserted into the drive unit 8 from one side along the axis 16 in order to couple the instrument 30 with the drive unit 8.

In the coupled state of the instrument 30, the support element 45 rests against a correspondingly formed stop 39 in the housing 15 of the drive unit 8. The stop 39 is mounted resiliently in the housing 15 and generates a pre-tensioning force on the instrument 30.

The side of the housing 15 opposite the stop 39 has a further stop 40 against which the base element 46 of the instrument 30 rests in the coupled state. The stop 40 is also preferably conical in form, corresponding to the base element 46.

The stops 39 and 40 prevent the instrument 30 from slipping through in an axial direction. The conical design of the two stops 39 and 40 as well as of the support and base elements 45 and 46 of the instrument 30 creates a specifically defined plug-in position of the instrument 30 in an axial direction and in a radial direction with respect to the axis 16. As FIG. 2 shows, a coaxial alignment of a longitudinal axis 38 extending through the instrument 30 with the axis 16 extending through the drive unit 8 can thus be achieved.

A retaining element 58 is preferably provided on the housing 15 which fixes the instrument 30 detachably with the housing 15, in order, in the coupled state, to prevent a rotation of the base element 46 in relation to the housing 15 or an axial slippage within the drive unit 8 along the axis 16. The retaining element 58 can comprise a magnet which exerts a holding force on the base element 46, which is made of ferromagnetic material.

Four identical drive modules 18 are built into the drive unit 8. The first drive module comprises a magnetic ring 21 driven by a motor 11, the second drive module comprises a magnetic ring 22 driven by a motor 12, the third drive module comprises a magnetic ring 23 driven by a motor 13 and the fourth drive module comprises a magnetic ring 24 driven by a motor 14. The magnetic rings each comprise a hollow-cylindrical inner section fitted with magnets 25 and an outer section in the form of a gear rim 28 projecting radially from the inner section. All four magnetic rings 21, 22, 23 and 24 are mounted in the housing 15 with, in each case, at least one roller bearing 29, in this case with two roller bearings 29, one on each side of the outer section.

Figure 5:
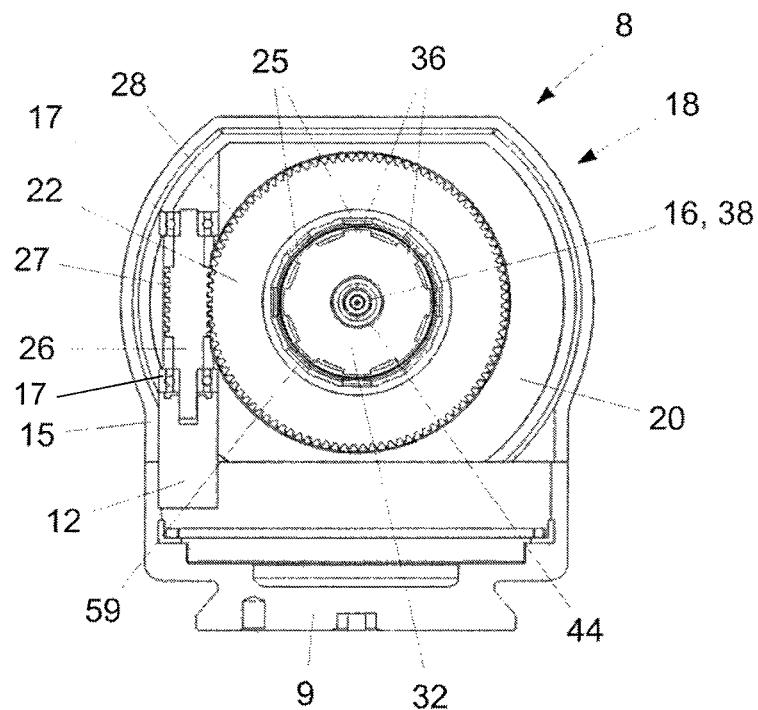
FIG. 5 shows a cross section through a drive module of the drive unit.

To represent all four drive modules 18, FIG. 5 shows their structure and functional principle with reference to the example of the second drive module 18. The drive module 18 has a stable mounting segment 20. The motor 12 is firmly connected with the mounting segment 20 and drives a gear 26.

The gear 26 is in this case designed as a worm gear and has a worm 27 which engages with the gear rim 28. The worm 27 is mounted rotatably in relation to the mounting segment 20 by means of bearings 17 and transmits the torque generated by the motor 12 to the magnetic ring 22 in order to drive it in a rotary manner around the axis 16. The magnetic ring 22 thus functions as a worm wheel and is connected with the motor 12 in a mechanically force-transmitting manner.

As can be seen in FIG. 3, the individual drive modules 18 are plug-connected together via their mounting segments 20, in that each mounting segment 20 has a projection on its right-hand side, as seen in FIG. 3, which engages into a complementary recess in the adjacent mounting segment 20 on the right, so that the gear rims 28 are flanked to the right and left by different mounting segments 20. On the one hand, the plugged connection permits a modular structure and a fixed alignment of the mounting segments 20 in relation to one another. On the other hand, the mounting segments 20 serve the purpose of fixing to the housing 15 of the drive unit 8, with which they can for example be screwed or also plugged together.

The four drive modules 18 are arranged next to one another and aligned coaxially in relation to one another, so that each magnetic ring 21, 22, 23 and 24 can rotate around the common axis 16. Motors of the four drive modules 18 can be actuated individually, so that the magnetic rings 21, 22, 23 and 24 can be rotated independently of one another.

When a magnetic ring 21, 22, 23, 24 rotates, the magnets 25 fixed to the magnetic ring in question rotate with it. Permanent magnets are preferably used as magnets 25. Alternatively, electromagnets can also be used.

Each of the four wheels 31, 32, 33, 34 of the actuation unit 19 of the instrument 30 is arranged concentrically to the longitudinal axis 38 of the instrument 30 and is surrounded by a magnetic ring 21, 22, 23 or 24 when the instrument 30 is coupled with the drive unit 8, i.e. the magnetic ring 21 is arranged concentrically around the wheel 31, the magnetic ring 22 is arranged concentrically around the wheel 32 and so on. (see FIGS. 2 and 4).

Each wheel 31, 32, 33, 34 has on its periphery a driving-force-transmitting structure in the form of several ferromagnetic bodies 36 which form a magnetic positive connection with the magnets 25. The motor-driven magnetic rings 21, 22, 23 and 24 therefore serve on the one hand to couple the instrument 30 detachably with the drive unit 8 and on the other hand to transmit torques to a wheel 31, 32, 33 and 34 of the actuation unit 19 of the instrument 30 corresponding to the respective magnetic ring 21, 22, 23 and 24, i.e. each magnetic ring 21, 22, 23, 24 is in magnetic force-transmitting connection with a corresponding wheel 31, 32, 33, 34.

FIG. 6 shows the actuation unit 19 of the instrument 30 in cross section. Every two of the four wheels 31, 32, 33, 34 are connected with one another via a roller bearing 47, so as to rotate around the longitudinal axis 38, and are arranged next to one another at a fixed distance. The left-hand outer wheel 31 is rotatably supported on the base element 46 by a bearing 47 pressed onto the base element 46. The right-hand outer wheel 34 is supported on the support element 45 by a bearing 47 pressed into the support element 45.

In the bearings 47 arranged between two wheels 31, 32, 33, 34, an outer ring of the bearing 47 is pressed into one of the wheels 31, 32, 33, 34 and an inner ring of the bearing 47 is pressed onto the other wheel 31, 32, 33, 34.

The bearings 47 arranged on each side of the wheels 31, 32, 33, 34 ensure the axial integrity of the construction elements connected by the bearings 47.

As shown in FIG. 6, the ferromagnetic bodies 36 can overlap the bearings 47 in an axial direction in order to make optimal use of the surface area available on the periphery of a wheel.

The wheel 32 adjacent the left-hand wheel 31 is connected, non-rotatably, with a first shaft 42. The non-rotatable connection is in the form of a tongue-groove connection with a tongue 55 connected with the first shaft 42 and a groove 54 formed in the wheel 32 and makes possible an axial relative movement as well as a transmission of a torque between the first shaft 42 and the wheel 32. The tongue 55 can, as in this case, be part of a right-hand sleeve 52 with which the first shaft 42 is firmly connected. Instead of the tongue-groove connection, a splined shaft connection, for example, could also be selected.

The first shaft 42 engages in an inner thread 53 of the wheel 33 adjacent the right-hand wheel 34 by means of an outer thread 56. The outer thread 56 is located on the sleeve 52 firmly connected with the first shaft 42.

The outer thread 56 and the inner thread 53 form a screw thread which converts a rotary movement of the second wheel 33 into a translatory movement of the first shaft 42 along the longitudinal axis 38. The pitch of the thread determines the transmission ratio and thus the advance per rotation.

The difference in the lengths of the groove 54 and tongue 55 determines the axial freedom of movement of the first shaft 42. Alternatively, other rotary-translatory conversion gears can be selected, for example a ball screw drive.

The two wheels 32, 33 interact such that, when one of the two wheels 32, 33 rotates, the first shaft 42 performs a translatory or axial movement along the longitudinal axis 38, and when both wheels 32, 33 rotate simultaneously it performs a rotary movement around the longitudinal axis 38.

The wheel 34 is firmly connected with the shaft sleeve 44, which is arranged coaxially with the first shaft 42 and surrounds it. Through rotation of the third wheel 34, the shaft sleeve 44 is driven and rotates relative to the first shaft 42 around the longitudinal axis 38. The end effector 60, connected with the shaft sleeve 44 by means of the swivel mechanism 79, is also rotated around the longitudinal axis 38.

A second shaft 41 is arranged, coaxially with the longitudinal axis 38, within the first shaft 42, which in this case is hollow throughout. The second shaft 41 is connected with the first shaft 42, rotatably but in an axially fixed manner, by means of (roller) bearings 49; i.e. a relative movement between the first and second shafts 41, 42 is only possible through a rotary movement, but not through an axial movement. The second shaft 41 can thus rotate relative to the first shaft 42 around the common longitudinal axis 38 and in the event of an axial movement of the first shaft 42, it is carried along by the latter, so that the second shaft 41 always moves together with the first shaft 42 in an axial direction, but can rotate independently of the latter.

The second shaft 41 is connected non-rotatably with the wheel 31. The non-rotatable connection is in the form of a tongue and groove connection, a tongue 50 being connected with the second shaft 41 and a groove 48 being formed in the wheel 31, and makes possible an axial relative movement of the second shaft 41 and the wheel 31 as well as a transmission of a torque between them. Where, in the event of an axial movement of the first shaft 42, the second shaft 41 is carried along by the latter, the second shaft 41 can move freely in the wheel 31 in an axial direction.

The tongue 50 can, as in this case, be part of a left-hand sleeve 51 with which the second shaft 41 is firmly connected. Instead of the tongue-groove connection, a splined shaft connection, for example, could also be selected. The difference in the lengths of the groove 48 and tongue 50 determines the axial freedom of movement of the second shaft 41. Since the first and second shafts move together in an axial direction, the difference in the lengths of the groove 48 and tongue 50 is the same as the difference in the lengths of the groove 54 and tongue 55.

The end effector 60 located on the distal end of the instrument 30 is swivelably connected with the shaft sleeve 44 via a swivel mechanism 79. The swivel mechanism 79 comprises a proximal member 61, which is firmly connected with the shaft sleeve 44. In a further development of the invention, the proximal member 61 and the shaft sleeve 44 can be formed as a single piece.

A distal member 62 of the swivel mechanism 79, which is coupled onto a base 63 of the end effector 60, is swivelably connected to the proximal member 61.

The swivelable connection of the proximal and distal members 61 and 62 can comprise any form of swivel bearing in which the proximal member 61 serves as a thrust bearing of the distal member 62. As FIG. 7 (with concealed edges) and FIG. 8 (without concealed edges) show, in this exemplary embodiment a guide slot system is chosen as swivel bearing, in which a guide slot 72 is formed in the proximal member 61 and a guide slot 75 is formed in the distal member 62.

A guide slot 72, 75 of the member 61, 62 interacts with a bolt 73, 74 fixed to the other member 62, 61, in that the course of the guide slot 72, 75 serves as a guide for the bolt 73, 74. At least one of the guide slots 72, 75 has a course which is not parallel with the longitudinal axis 38 of the instrument 30. The course is preferably linear, but can, alternatively, also be curved.

In the event of a relative movement of the distal member 62 the bolts 73, 74 guided in the guide slots 72, 75 follow the course of the guide slots and cause the distal member 62 to swivel accordingly, whereby an end effector axis 76 extending longitudinally through the end effector 60 is oriented at an angle in relation to the longitudinal axis 38 of the instrument 30. As shown in FIG. 9, the swivelling movement takes place around a swivel axis 78 which runs normally to the longitudinal axis 38. The end effector 60 coupled onto the distal member 62 swivels with it, accordingly.

The end effector 60 can swivel in the direction shown in FIG. 9 or in a direction opposite thereto (as shown in FIG. 8). The swivelling movement in one direction or in the opposite direction is in each case performed around a swivel axis which extends normally to a parallel of the longitudinal axis 38. In FIG. 9 the end effector 60 swivels around the swivel axis 78, in FIG. 8 it swivels around a swivel axis (not shown) located at a distance from and running parallel to the swivel axis 78.

In an alternative embodiment of the invention, the swivel mechanism can be realised with only a single guide slot system in which a guide slot is recessed either into the proximal member or into the distal member and in each case interacts with a bolt of the other member and the bolt has a cross section, elongated in the direction of the guide slot, which engages, non-rotatably, in the guide slot.

The first shaft 42 and the second shaft 41 have at least one flexible partial region. This partial region extends through the swivel mechanism 79 and makes it possible for the first shaft 42 and the second shaft 41 to follow a swivelling movement of the distal member 62, swivelling accordingly. The flexible partial region of the two shafts 41, 42 is preferably elastically deformable.

As FIG. 9 shows, the distal end of the first shaft 42 is firmly connected with the base 63 of the end effector 60. Thus, the base 63 of the end effector 60 can be moved by means of the first shaft 42. If the first shaft 42 is driven in a rotary movement, then the base 63 is rotated relative to the swivel mechanism 79 around the end effector axis 76.

If the first shaft 42 is driven in an axial direction, then the base 63 of the end effector 60 is also moved in an axial direction, whereby the distal member 62 of the swivel mechanism 79 connected with the base 63 is at the same time displaced along the guide slot 72 or 75 and performs a swivelling movement around the swivel axis 78, i.e. the end effector 60 can be swivelled through an axial movement of the first shaft 42.

If the shaft sleeve 44 is driven in a rotary movement, the swivel mechanism 79 rotates together with the end effector 60 around the longitudinal axis 38.

The end effector is designed according to the intended purpose of the instrument 30 (e.g. industrial or surgical application) and comprises for example a camera, a light source, a blade, a welding electrode or any other type of tool. In this exemplary embodiment, the end effector 60 is designed as a gripping tool and has two grippers 64 and 65, each of which is connected with the base 63 so as to be rotatable around a gripper axis 68.

The base 63 is connected with the distal member 62 of the swivel mechanism 79 so as to be rotatable, by means of bearings 71, around the end effector axis 76 extending through the distal member 62 and the base 63.

Each of the grippers 64 and 65 is connected with a positioning element 66. The connection is in the form of a guide slot system in which, preferably, each gripper 64 and 65 has a guide slot 70 and the positioning element 66 has a corresponding bolt 69. Alternatively, the reverse arrangement could be chosen.

The positioning element 66 is mounted so as to be axially displaceable along the end effector axis 76. The movement of the positioning element 66 is driven through the second shaft 41. For this purpose, a drive element 77 is attached at the distal end of the shaft 41 which engages with the positioning element 66 by means of screw threads 67. The screw thread 67 translates a rotary movement of the second shaft 41 into an axial movement of the positioning element 66 along the end effector axis 76.

Through a displacement of the positioning element 66, the bolts 69 are displaced along the end effector axis 76 and slide along the path defined by the guide slots 70. The bolts 69 thereby press laterally against the guide slots 70, so that, depending on the direction of movement of the positioning element 66, the grippers 64 and 65 are spread or closed together. Advantageously, the guide slots 70 are formed such that the grippers 64 and 65 are pressed together when the positioning element 66 is moved away from the base 63 and such that the grippers 64 and 65 are spread when the positioning element 66 is moved towards the base 63 in order that the forces acting from the bolt 69 onto the grippers 64, 65 are translated into the greatest possible clamping forces when the grippers 64, 65 are closed.

The guide slot 70 of each gripper 64, 65 and its gripper axis 68 are arranged such that the gripper axis 68 extends outside of the guide slot 70 of the guide slot system. This prevents the bolt 69 guided in the guide slot 70 of the gripper 64, 65 from being able to assume a position which coincides with the gripper axis 68 of the gripper 64, 65, i.e. the gripper axis 68 and bolt 69 are always spaced apart, so that the force acting on the bolt 69 always generates a torque around the gripper axis 68.

As shown in FIG. 9, the guide slot 70 can be located next to a plane, perpendicular to the end effector axis 76, in which the gripper axes 68 of the grippers 64, 65 extend, without intersecting this plane. In this exemplary embodiment, the guide slots 70 extend between this plane and a clamping zone or the tip of their respective gripper 64, 65, in order to make the best use of the available construction space in the grippers 64, 65.

In order for the greatest possible torque to be applied at the grippers 64, 65 as they close, in the closed state of the grippers 64, 65 the bolts 69 must assume a position in the guide slots 70 in which the distance between bolts 69 and gripper axis 68 of a gripper 64, 65 is at a maximum. For this purpose, the guide slots 70 of each gripper 64, 65 are designed such that the distance between an end of the guide slot 70 facing the gripper axis 68 and the end effector axis 76 is less than the distance between an end of the guide slot 70 facing away from the gripper axis 68 and the end effector axis 76. In this case the grippers 64, 65 are closed when the bolts 69 are moved away from the gripper axes 68 and towards the clamping zone of the grippers 64, 65.

In order to provide the end effector 60 with good stability, in addition to being compact, a cut-out 80 is provided in the positioning element 66 for each gripper 64, 65, as shown in FIG. 11. On the one hand, the bolts 69 are held in the positioning element 66 on both sides of their respective cut-out 80, so that the cut-outs 80 form an accommodation for the bolts 69. On the other hand, the grippers 64, 65 can, in the closed state, be supported against a lateral contact surface of the cut-out 80. This prevents the grippers 64, 65 from bending away to the side when holding a heavy load. In addition, this accommodation of the grippers 64, 65 prevents the bolts 68 from slipping out of their guide slots 70.

A continuous channel 43 can be integrated within the instrument 30 which can be used to convey media, for example to rinse the end effector 60 or the object which is to be gripped by the end effector 60 or to deliver gas. The channel 43 is preferably formed by a cavity in the second shaft 41, as shown in FIGS. 6 and 9.

The instrument 30 can also have on the proximal end a handle 37 connected non-rotatably with the second shaft 41 (see FIGS. 4 and 6). This handle 37 can be used to insert the instrument 30 into the drive unit 8 or remove it. Through manual rotation of the handle 37 the second shaft 41 can be actuated which—as explained above—controls the grippers. This allows the user to open the grippers 64, 65 manually via the drive unit 8 in the event of a malfunction of the motor drive.

FIG. 10 summarises the individual actuation possibilities in table form and once again illustrates the functional principle of the wheels 31, 32, 33 and 34, the shaft sleeve 44 and the shafts 41 and 42 as well as their effects on the actuation of the end effector 60. A distinction is made between the following forms of actuation: actuation of the grippers 64, 65 (see FIG. 11); swivelling of the end effector 60 around the swivel axis 78 (see FIGS. 8 and 9); rotation of the end effector 60 around the end effector axis 76 (see FIG. 12) and rotation of the swivel mechanism 79 together with the end effector 60 around the longitudinal axis 38 (see FIG. 13). The wheels which must be driven in order to perform the relevant actuation are marked with an "X". The movement of the shaft sleeve or the shafts effected by the driven wheels are marked "R" or "A", wherein "R" defines a rotary movement and "A" defines an axial movement.

Accordingly, the second shaft 41 is rotated through rotation of the fourth wheel 31 alone. The direction of rotation of the second shaft 41 determines whether the positioning element 66 is moved towards or away from the base 63 and, accordingly, causes the grippers 64 and 65 to open or close.

Through rotation of the second wheel 33, the first shaft 42 is shifted in an axial direction. The second shaft 41 is carried along by the first shaft 42 and is thus also shifted axially. The axial movement of the first shaft 42 causes a displacement of the base of the end effector 60 which is superimposed on a swivelling movement, around the swivel axis 78, of the distal member 62 of the swivel mechanism 79 connected with the base 63.

In order to rotate the end effector 60 in relation to the swivel mechanism 79, around the end effector axis 76, the first shaft 42 is caused to rotate through synchronous rotation of the first and second wheels 32 and 33. In order to prevent an adjusting movement of the positioning element 66, which would trigger an actuation of the grippers 64 and 65 caused through the difference in rotational speed between the first and second shaft 41, 42, the second shaft 41 is rotated synchronously with the first shaft 42 by driving the fourth wheel 31.

By driving of the third wheel 34, the shaft sleeve 44 and thus the swivel mechanism 79 connected with it is rotated around the longitudinal axis 38. In order also to rotate the end effector 60 together with the swivel mechanism 79, all the wheels 31 to 34 can be driven simultaneously, so that the two shafts 41 and 42 rotate together with the shaft sleeve 44.

FIGS. 14 to 16 show alternative embodiments of the swivel mechanism 79. In the embodiment shown in FIG. 7 the guide slot 72 of the proximal member 61 extends non-parallel or at an angle to the longitudinal axis 38 of the instrument 30 and the guide slot 75 of the distal member 62 extends non-parallel or at an angle to the end effector axis 76. In contrast, FIG. 14 shows a swivel mechanism 79, wherein one of the guide slots 72, 75 extends parallel to one of the axes 38, 76; in this case then, the guide slot 75 of the distal member 62 extends parallel to the end effector axis 76.

In contrast to FIG. 7, FIG. 15 shows a swivel mechanism 79, wherein the bolts 73 and 74 are arranged in one member 62 and the guide slots 72 and 75 are arranged on the other member 61. In this variant the two bolts 73 and 74 are thus always at the same distance from one another.

FIG. 16 shows a swivel mechanism 79 with only one guide slot 72 and only one bolt 73. Since in this case the bolt 73 is wider than in FIG. 7, it can be supported on its own, non-rotatably, against the guide slot 72, i.e. the second guide slot system for supporting the torque of the distal member 62 on the proximal member 61 can thus be dispensed with.

REFERENCE NUMBERS 1 attachment element
2 joint
3 joint
4 joint
5 arm element
6 arm element
7 input device
8 drive unit
9 flange
10 robot
11 motor
12 motor
13 motor
14 motor
15 housing
16 axis
17 bearing
18 drive module
19 actuation unit
20 mounting segment
21 first magnetic ring
22 second magnetic ring
23 third magnetic ring
24 fourth magnetic ring
25 magnet
26 (worm) gear
27 worm
28 gear rim
29 roller bearing
30 instrument
31 fourth wheel
32 first wheel
33 second wheel
34 third wheel
36 ferromagnetic body
37 handle
38 longitudinal axis
39 stop
40 stop
41 second shaft
42 first shaft
43 channel
44 shaft sleeve
45 support element
46 base element
47 (roller) bearing
48 groove
49 bearing
50 tongue
51 sleeve
52 sleeve
53 inner thread
54 groove
55 tongue
56 outer thread
58 retaining element
59 barrier
60 end effector
61 proximal member
62 distal member
63 base
64 first gripper
65 second gripper
66 positioning element
67 screw thread
68 gripper axis
69 bolt
70 guide slot
71 bearing
72 guide slot
73 bolt
74 bolt
75 guide slot
76 end effector axis
77 drive element
78 swivel axis
79 swivel mechanism
80 section

The invention claimed is:

1. An instrument (30) with an elongated first hollow shaft (42), an end effector (60) which is arranged on a distal end of the first hollow shaft (42), and an actuation unit (19) arranged on a proximal end of the first hollow shaft (42), wherein the actuation unit (19) comprises a first wheel (32) which is connected non-rotatably with the first hollow shaft (42), characterised in that the first hollow shaft (42) is axially displaceable in relation to the first wheel (32) and is in threaded engagement with a second wheel (33) adjacent the first wheel (32), and wherein the second wheel (33) is axially non-displaceable in relation to the first wheel (32), and further including a second shaft (41) disposed within the hollow first shaft (42) and configured to drive a working movement of the end effector (60), and wherein the second shaft (41) is coupled to a fourth wheel (31) of the actuation unit (19).

2. The instrument (30) according to claim 1, characterised in that the first shaft (42) extends through a shaft sleeve (44) which is connected, at a proximal end, rotatably and axially immovably, with one of the wheels (32, 33) and that the end effector (60) is coupled on the distal ends of the first shaft (42) and the shaft sleeve (44) in order to swivel around a swivel axis (78) oriented transversely to the shaft sleeve (44) by means of a swivel mechanism (79) and is driven through a relative movement between the first shaft (42) and shaft sleeve (44).

3. The instrument (30) according to claim 2, characterised in that the shaft (42) has a flexible region which extends at least partially through the swivel mechanism (79).

4. The instrument (30) according to claim 2, characterised in that the end effector (60) is rotatable around an axis of rotation (76) which is swivelable around the swivel axis (78), and the rotation is controlled through a rotation of the first shaft (42).

5. The instrument (30) according to claim 2, characterised in that the swivel mechanism (79) comprises a proximal member (61) firmly connected with the distal end of the shaft sleeve (44) and a distal member (62) connected with the first shaft (42) which is driven in a swivelling action through an axial displacement of the first shaft (42) relative to the proximal member (61).

6. The instrument (30) according to claim 5, characterised in that each the two members (61, 62) has a bolt (73, 74) and a guide slot (72, 75) in which a bolt (73, 74) of the other member is displaceable in order to guide the swivelling movement of the distal member (62).

7. The instrument (30) according to claim 2, characterised in that the actuation unit (19) comprises a third wheel (34) which is connected, non-rotatably and axially immovably, with the shaft sleeve (44).

8. The instrument (30) according to claim 1, characterised in that the second shaft (41) is coupled non-rotatably to the fourth wheel (31) and is axially displaceable together with the first shaft (42).

9. The instrument (30) according to claim 1, characterised in that the second shaft (41) has a flexible region which extends at least partially through the swivel mechanism.

10. The instrument (30) according to claim 1, characterised in that at least two wheels (31, 32, 33, 34) of the actuation unit (19) are coupled together via a roller bearing (47) and are mounted so as to be axially immovable relative to one another.

11. The instrument (30) according to claim 10, characterised in that the roller bearing (47) is a radial bearing, an outer ring of which is accommodated in one of the two wheels (31, 32, 33, 34) and an inner ring of which is pushed onto the other wheel (31, 32, 33, 34).

12. The instrument (30) according to claim 10, characterised in that a plurality of driving-force-transmitting elements (36) are distributed on the periphery of one of the wheels (31, 32, 33, 34) which transmits a driving force overlaps axially with the roller bearing (47).

13. The instrument (30) according to claim 1, wherein said instrument further includes a third wheel (34) and a fourth wheel (31), said instrument characterised in that at least one of the wheels (31, 32, 33, 34) is equipped with ferromagnetic bodies (36) on its periphery.

14. The instrument (30) according to claim 1, characterised in that the actuation unit (19) is enclosed by a germ-proof, sleeve-formed barrier (59).

15. The instrument (30) according to claim 1, characterised in that the actuation unit (19) is configured to be pushed, releasably, in the longitudinal direction of the shaft (42), into a cavity of a drive unit (8).

16. The instrument (30) according to claim 15, characterised in that the drive unit (8) includes a plurality of drive modules (18) arranged in a staggered manner in the longitudinal direction, and wherein each of said plurality of drive wheels interacts with a respective one of the wheels (31, 32, 33, 34).

17. The instrument (30) according to claim 1, characterised in that the actuation unit (19) includes at least one motor drive which drives at least one of the wheels (31, 32, 33, 34).

* * * * *